United States Patent [19]
Reid et al.

[11] Patent Number: 5,635,360
[45] Date of Patent: Jun. 3, 1997

[54] IMMUNOASSAY FOR HUMAN RESTRICTIN

[75] Inventors: Robert A. Reid, Durham; Rhonda L. Ackley, Chapel Hill; John J. Hemperly, Apex, all of N.C.

[73] Assignee: Becton, Dickinson and Company, Franklin Lakes, N.J.

[21] Appl. No.: 404,671

[22] Filed: Mar. 15, 1995

[51] Int. Cl.$^6$ ........................................ G01N 33/53
[52] U.S. Cl. .................. 435/7.21; 435/7.1; 435/7.2; 436/501; 530/387.9; 530/388.2; 530/388.22; 530/388.85; 530/389.1
[58] Field of Search ..................... 435/7.1, 7.2, 7.21; 436/501; 530/387.9, 388.2, 388.22, 388.85, 389.1

[56] References Cited

PUBLICATIONS

L. Vaughan, et al. "Tenascin–Contactin/F11 Interactions: A Clue for A Developmental Role?" *Persp. Dev. Neurobiol.* 2:43–52 (1994).

M. Schachner, et al. "The Perplexiing Multifunctionality of Janusin, a Tenascin–Related Molecule" *Perp. Dev. Neurobiol.* 2:33–41 (1994).

R. Chiquet–Ehrismann, et al. "The Tenascin Gene Family" *Perp. Dev. Neurobiol.* 2:3–7 (1994).

F. G. Rathjen, et al. "Restrictin: a chick neural extracellular matrix protein involved in cell attachment copurifies with the cell recognition molecule F11" *Development* 113:151–164 (1991).

A. Lochter, et al. "The Extracellular Matrix Molecule Janusin Regulates Neuronal Morphology in a Substrate–and Culture Time–dependent Manner" *Euro. J. Neurosci.* 6:597–606 (1994).

P. Pesheva, et al. "Tenascin–R (J1 160/180) inhibits fibronectin–mediated cell adhesion—funtional relatedness to tenascin–C" *J. Cell Sci.* 107:2323–2333 (1994).

A. Faissner, et al. "Binding of the J1 Adhesion Molecules to Extracellular Matrix Constituents" *J. Neurochem.* 54:1004–1015 (1990).

B. Fuss, et al. "Identification of a cDNA Clone Specific for the Oligodendrocyte–Derived Repulsive Extracellular Matrix Molecule J1–160/180" *J. Neurosci. Res.* 29:299–307 (1991).

B. Fuss, et al. "Molecular Characterization and In Situ mRNA Localization of the Neural Recognition Molecule J1–160/180: a Modular Structure Similar to Tenascin" *J. Cell Biol.* 120:1237–1249 (1993).

U. Norenberg, et al. "The Chicken Neural Extracellular Matrix Molecule Restrictin: Similarity with EGF–, Fibronectin Type III–, and Fibrinogen–like Motifs" *Neuron* 8:849–863 (1992).

Chiquet–Ehrismann et al., Experimentia, 51, pp. 853–862 (1995) "Tenascins, a growing body of extracellular matrix proteins".

Gherzi et al. J. Biol. Chem., 270, #7, pp. 3429–3434 (1995) "Human Tenascin Gene".

*Primary Examiner*—Lora M. Green
*Attorney, Agent, or Firm*—Donna R. Fugit

[57] ABSTRACT

Human restrictin proteins and nucleic acid sequences encoding them are provided. Antibodies which recognize human restrictin in human brain are disclosed. In the human brain, restrictin occurs as two major polypeptides of 180 and 160 kD located in fiber tracts. These polypeptides are similar to those seen in rat brain. Surprisingly, restrictin has also been found in the peripheral nerves of rats and humans The antibodies also detect a 170 kD polypeptide in MATRIGEL, an extracellular matrix product of rat EHS sarcoma cells widely used as a tissue culture substrate. Monoclonal antibodies to human restrictin and assays using the human restrictin protein, antibodies and DNA sequences are also provided.

3 Claims, 1 Drawing Sheet

IMMUNOASSAY FOR HUMAN RESTRICTIN

FIELD OF THE INVENTION

The present invention relates to extracellular matrix molecules and nucleic acid sequence encoding them.

BACKGROUND OF THE INVENTION

The adherence of cells to each other and to the extracellular matrix, as well as the cellular signals transduced as a consequence of such binding, are of fundamental importance to the development and maintenance of body form and function. A number of molecules mediating cell adhesion have been identified and characterized at the molecular level both in vertebrates and in invertebrates. Many cell surface cell adhesion molecules (CAMs) are of three major types: 1) members of the immunoglobulin supergene family, which mediate calcium independent adhesion, 2) cadherins, which mediate calcium-dependent adhesion and are important structural components of adherence junctions, and 3) integrins, a family of heterodimeric proteins which can facilitate adhesion of cells both to each other and to the extracellular matrix.

CAMs may have multiple ligands. They can mediate adhesion by the interaction of a CAM on one cell with the identical CAM on another cell (homophilic binding), or they can mediate adhesion by interacting with different CAMs or extracellular matrix molecules (heterophilic binding). For example, contactin, a member of the immunoglobulin gene superfamily can undergo homophilic binding or can bind heterophilically to other cell surface molecules such as the L1 antigen or to extracellular matrix molecules of the tenascin family. One extracellular matrix ligand for contactin is janusin, which is a member of the tenascin-R family. Janusin is closely related to tenascin in its patterns of epidermal growth factor, fibronectin type III and fibrinogen-like domains. In rodents, it is synthesized by oligodendrocytes and subpopulations of neurons at late developmental stages in the central nervous system. It can promote cell adhesion or anti-adhesion, depending on the neural cell type with which it interacts, promoting neurite outgrowth of some neural cell types and inhibiting neurite outgrowth from other neuronal populations. The repulsive response of neurons to janusin may be mediated by contactin. Janusin has been identified in rodents (A. Faissner, et al. 1990. *J. Neurochem.* 54: 1004–1015) and the rat gene has been cloned (B. Fuss, et al. 1991. *J. Neurosci. Res.* 29: 299–307) and sequenced (B. Fuss, et al. 1993. *J. Cell Biol.* 120: 1237–1249) The chicken homolog of janusin, referred to as restrictin, has also been identified and characterized (U. Norenberg, et al. 1992. *Neuron* 8: 849–863).

SUMMARY OF THE INVENTION

Prior to the present invention, no human homolog of janusin/restrictin had been identified and it was not previously known if such a homolog existed. A human homolog of rat janusin has now been found, and the complete cDNA sequence encoding it has been determined. Antisera were prepared against a fragment of the human restrictin protein expressed in bacteria. These antibodies detect the immunogen, high molecular weight polypeptides in human brain, and cross react with several animal species. In the human brain, restrictin occurs as two major polypeptides of 180 and 160 kD located in fiber tracts. These polypeptides are similar in size to those seen in rat brain. Surprisingly, restrictin has also been found in the peripheral nerves of rats and humans. The antibodies also detect a 170 kD polypeptide in MATRIGEL, an extracellular matrix product of rat EHS sarcoma cells widely used as a tissue culture substrate. Monoclonal antibodies to human restrictin and assays using the human restrictin protein, antibodies and DNA sequences are also provided.

Figure 1:
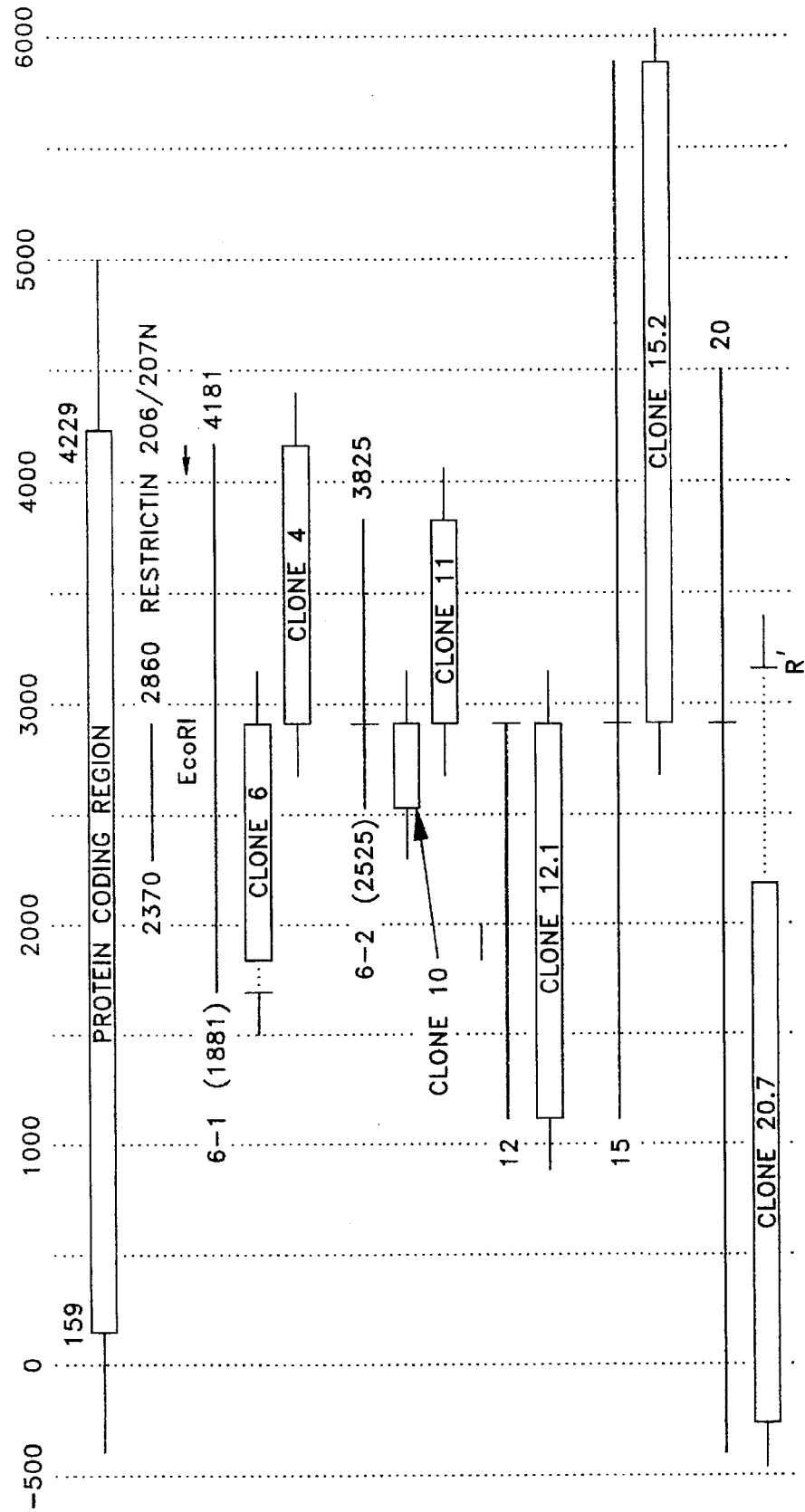
FIG. 1 illustrates the cloning process used to obtain the human restrictin cDNA sequence.

DETAILED DESCRIPTION OF THE INVENTION cDNAs encoding human restrictin were cloned from human brain polyA+RNA using the reverse transcriptase polymerase chain reaction (RT-PCR) with primers based on the rat janusin gene sequence. RT-PCR was performed on rat and human (adult and fetal, Clontech) brain polyA+ RNA using the one-step protocol described by Goblet, et al. (1989. Nucl. Acids Res. 17: 2144). PolyA+ RNA (1 µg) and 300 ng of each primer (see below) in 66 µl DEPC water were incubated at 65° C. for 15 min. and cooled on ice. Thirty-three µl of 3X RT-PCR reagent mix (3X PCR buffer, 150 mM KCl, 30 mM Tris-HCl pH 8.3, 4.5 mM $MgCl_2$, 0.3% gelatin, 500 µM dNTPs, 200 U M-MLV reverse transcriptase, 4 U rRNAsin (Promega, Madison. Wis.), 2.5 U AMPLITAQ (Perkin-Elmer Cetus, Norwalk, Conn.) was added and the reaction was incubated at 37° C. for 30 min. The amplification reaction (94° C. for 1 min., 50° C. for 2 min., and 72° C. for 2 min.) was repeated for 40 cycles. The primer pair for amplification was as follows:

5'-ACTGACAGATCTAGAGCC SEQ ID NO: 1
(corresponding to nucleotides 2375-2392 in rat)

5'-GGTGGTCGATAGGATACT SEQ ID NO: 2
(corresponding to nucleotides 2856-2839 in rat)

A major 480 bp amplification product was obtained from rat RNA, which was subcloned and sequenced, confirming that this product corresponded to rat janusin. A minor 290 bp product was also obtained in rat. An amplification product of the appropriate size (480 bp) was also generated from human adult brain RNA. This product was subcloned and sequenced directly (Mihovilovic, 1989). Amplification of fetal RNA produced only a 290 bp amplification product which was subsequently found not to be human restrictin.

The 480 bp human amplification product (206/207N) was used as a probe on Northern blots of multiple regions of human brain (Clontech). The radiolabeled probe was prepared using a random primer labeling kit (BRL. Gaithersburg, Md.) with purification over NICK columns (Pharmacia, Piscataway, N.J.). Blots were reprobed with a human beta-actin probe (Clontech) to determine the relative amounts and integrity of RNA in each sample. The probe hybridized to a single approximately 12 Kb nucleic acid sequence in amygdala, caudate nucleus, corpus collusum, hippocampus, hypothalamus, substantia nigra, subthalamic nuclei and thalamus. The restrictin cDNA clones described below were also used as probes on northern blots of human fetal tissues. The approximately 12 Kb restrictin mRNA seen in adult brain was also detected in fetal brain, but was absent from fetal heart, lung, liver and kidney. This illustrates the tissue specificity of restrictin.

Two commercially available lambda human cDNA libraries were screened as recommended by the manufacturer using 206/207N as a probe to identify additional clones for determination of the sequence of the full-length human restrictin gene (FIG. 1). Initial screening with 206/207N identified cDNA clones 6-1 and 6-2. A second hybridization screening using a probe from the 5' end of clone 6-1, as illustrated in FIG. 1, produced cDNA clones 12 and 15. The upstream end of clone 12 was used in a third library screen to isolate clone 20 Together, these clones encode the entire protein coding region of human restrictin (FIG. 1). The lambda cDNA inserts of these clones were either 1) PCR amplified using lambda gt10 EcoRI forward and reverse primers for direct sequencing as described above (Mihovilovic, 1989), or 2) subcloned into pBLUESCRIPT (SK+) (Stratagene, La Jolla, Calif.) for sequencing by dye-termination or dye-labeled primer methods (Applied Biosystems, Model 373A, Foster City, Calif.). Sequencing primers were synthesized on an Applied Biosystems (ABI) Model 380B DNA synthesizer and purified using OPC cartridges (ABI). Sequence alignments, translations, and feature location were performed using IG-Suite software (Intelligenetics, Mountain View, Calif.). In this manner, the entire 4,724 bp human restrictin cDNA coding sequence was determined by sequencing both strands of the cDNAs (SEQ ID NO: 3). The sequence of the full-length restrictin protein (1358 amino acids, SEQ ID NO: 4) was deduced from the cDNA sequence. The human restrictin protein shows structural similarity to other members of the tenascin-R family. In particular, human restrictin, like its homologs from rat and chicken, comprises a short amino terminal region followed by heptad repeats, epidermal growth factor-like repeats, nine fibronectin type III repeats and a carboxyl-terminal region homologous to the globular domain of fibrinogen. There is no evidence for a hydrophobic membrane spanning region, consistent with restrictin being a secreted, extracellular matrix molecule. The human sequence obtained is highly homologous to the rat and chicken sequences at both the DNA (88 and 76%, respectively, within the protein coding region) and at the amino acid level (93 and 72%, respectively).

SEQ ID NO: 3, a fragment of SEQ ID NO: 3, or an equivalent nucleic acid molecule which employs degenerate codons to encode the amino acid sequence of SEQ ID NO: 4 or a fragment thereof, may be cloned into an expression vector as is known in the art to produce recombinant human restrictin in transformed or transfected host cells. Recombinant human restrictin and recombinant human restrictin fragments provide a convenient source of these molecules for immunization, immunoassays, and use in tissue culture growth substrates. To generate antisera to human restrictin, the 206/207N fragment (nucleotides 2686–3165 of SEQ ID NO: 3 with EcoRI cloning sites at both the 5' and 3' ends) was subcloned into the EcoRI site of pGEX-3X (Pharmacia), producing a recombinant human restrictin-glutathione-S-transferase (GST) fusion protein for immunization. After transformation of E. coli, expression of the fusion protein was induced with IPTG and the soluble material was purified over a glutathione-S Sepharose affinity column. The purified material was used to immunize rabbits using standard methods. Sera were collected and assayed by immunoblotting against the immunogen and against the 206/207N protein fragment, expressed by subcloning into the pATH expression system (New England BioLabs). The anti-fusion protein antisera recognized both of these antigens on Western blots, but anti-chicken restrictin did not, indicating immunological differences between the human and chicken restrictin proteins.

To verify the reactivity of the antisera against human proteins, adult brain membranes were prepared and extracted. In brief, postsmortem human brain was Dounce homogenized into 0.32M sucrose, 5 mM EDTA, 20 mM Tris-HCl (pH 8) containing 1 mM PMSF, 0.5 mM p-chloromercuriphenylsulfonic acid and 5 µg/ml of aprotinin and leupeptin as protease inhibitors After centrifugation at 500×g for 30 min. to remove nuclei and cellular debris, the supernatant was centrifuged at 80,000×g to collect the membrane fraction, which was then extracted with 1% sodium deoxycholate in homogenization buffer for 1.5 hr. at 4° C. The detergent extract was clarified by centrifugation at 100,000×g and used subsequently for either SDS-PAGE directly or for further purification of a protein fraction bearing the HNK-1 epitope, which may be involved in binding cell adhesion molecules HNK-1 brain fractions were immunoaffinity enriched on anti-Leu7 (Becton Dickinson) coupled to Sepharose. Immunoblotting was performed using a PROTOBLOT AP system (Promega) as recommended by the manufacturer with an alkaline phosphatase-conjugated anti-rabbit IgG as the secondary antibody and color development using NBT/BCIP. In Western blots, the anti-fusion protein antisera routinely detected two bands of approximately 180 and 160 kD in human brain and in HNK-1 enriched fractions. These bands were apparently enriched in the latter. The reactivity of the antisera was inhibited in a concentration dependent manner by addition of the GST fusion protein, but not by addition of GST, indicating a specific immune reaction to the human restrictin fragment. Western blots of rat, mouse, cow, pig and chicken brain extracts demonstrated similar sized bands (180 kD and 160 kD) in all cases. There were, however, slight mobility shifts, possibly due to species variation in amino acid sequence or to differential glycosylation. MATRIGEL (Collaborative Biomedical Products), an extracellular matrix substrate derived from rat EHS sarcoma cells as an in vitro tissue culture growth substrate, was also reactive with the antiserum, revealing a 170 kD polypeptide.

For immunohistological studies, frozen human or rat tissues were sectioned and fixed using acetone or 4% paraformaldehyde. Staining was performed using the VECTA-STAIN ELITE ABC system (Vector Laboratories) as recommended. Primary anti-fusion protein antisera were used at a 1:1000 dilution. Paraffin sections were treated using the microwave antigen retrieval system (U.S. Pat. No. 5,244,787) before staining. The antisera were reactive with frozen sections of human peripheral nerve (peripheral nervous system), rat hippocampus (central nervous system) and human cerebellum (central nervous system) and with paraffin section human pons (central nervous system). In all cases, there were areas of clear positivity as well as areas that were clearly negative. For example, in the peripheral nerve experiments, the surrounding, non-neuronal tissue was unstained, and in the central nervous system, there were clearly unstained cells in all areas examined.

Antibodies according to the invention which recognize human restrictin are useful in methods for detecting the protein in immunoassay systems. Polyclonal antisera raised to human restrictin or to protein fragment of human restrictin may be used to detect the restrictin protein in immunoassay methods involving binding between the protein or fragment and the antibodies, e.g., ELISAs and immunoblots. These conventional immunoassay methods can be readily adapted to employ the antibodies and restrictin protein disclosed herein. Alternatively, monoclonal antibodies which recognize the human restrictin protein of the invention may be prepared using methods known in the art, such as that of Kohler and Milsrein (1975. Nature 256: 495) and used in immunoassays. The spleen cells of mice immunized with the human restrictin protein or a fragment thereof are fused with murine myeloma cells and the resulting hybridomas are screened against the immunogen to select those producing the desired anti-restrictin monoclonal antibody In general, binding between protein and antibody in an immunoassay is detected by inclusion of a detectable label in the reaction which generates a signal. The detectable label is usually conjugated to the antibody or protein and may be directly detectable (e.g., a dye, radioisotope or fluorochrome) or rendered detectable after further chemical reaction (e.g., an enzyme which reacts to produce a colored product, or biotin which may be bound to labeled avidin).

Polyclonal and monoclonal antibodies according to the invention may also be used to purify human restrictin from tissues, or to purify restrictin from the tissues of a cross-reacting species by immunoaffinity purification methods, e.g., immunoaffinity chromatography. This provides a source of natural restrictin for use in immunoassays, as an immunogen, or in tissue culture systems to promote or inhibit neurite outgrowth.

Oligonucleotides derived from the nucleotide sequences encoding human restrictin are useful in nucleic acid hybridization assays for detection of related restrictin nucleotide sequences. They may also be used as primers for amplification of restrictin target sequences. Oligonucleotide probes for hybridization according to the invention may comprise the complete coding sequence of the human restrictin cDNA or a portion thereof, such as nucleotides 2686–3165 of SEQ ID NO: 3. Primers are generally short portions of the nucleotide sequence which specifically hybridize to restrictin nucleotide sequences, allowing specific amplification. One skilled in the art will further recognize that oligonucleotide probes and primers may also be designed which comprise all or a portion of a sequence which is complementary to SEQ ID NO: 3. Detection of nucleic acids by hybridization to a probe is known in the art. Such methods as Southern blotting, Northern blotting, dot blotting, nucleic acid amplification methods and the like may be readily adapted to detection of nucleotide sequences containing all or part of the human restrictin coding sequence, or to detection of all or part of the restrictin coding sequence of a cross-reacting species. This is done using the nucleotide sequence given in SEQ ID NO: 3 to design appropriate probes and primers. For purposes of the present invention, the terms "encoding" and "coding for" are intended to include nucleic acids which comprise sequences which can be transcribed and/or translated to produce restrictin, or a fragment thereof, including degenerate nucleotide sequences. It will also be understood that probes and primers derived from the disclosed nucleotide sequences may also be used to detect fragments of restrictin coding sequences. Hybridization of the probe or amplification by the primers may be detected by means of a directly or indirectly detectable label associated with the probe or primer, i.e., incorporated into the probe or conjugated to it. In general, the same labels useful for labeling antibodies and antigens may be used to label oligonucleotides. In addition, it is within the ordinary skill in the art, given the nucleotide sequence of SEQ ID NO: 3, to derive the complementary nucleotide sequence, which may also be used to prepare probes and primers and which may be detected by use of probes and primers. Further, the present disclosure of SEQ ID NO: 3 allows derivation of RNA sequences which are complementary to SEQ ID NO: 3 or to the complement of SEQ ID NO: 3. Such equivalent RNA sequences may be detected by hybridization or amplification as well.

The reagents for performing these immunoassays, hybridization assays, and nucleic acid amplification may be conveniently packaged together for sale or use in the form of a kit. A kit for immunoassay may contain an antibody which recognizes and binds to restrictin. The antibody may be labeled, or a second antibody carrying the label may be included for detection of binding. Optionally, any reagent required for performing the assay and detecting the label may be included. A kit for hybridization assays or amplification may contain oligonucleotide probes or primers which hybridize to one or more nucleotide sequences contained in SEQ ID NO: 3. The probes or primers may be conjugated to a detectable label for detection. Optionally, the hybridization or amplification kit may contain any reagents required for performing the hybridization or amplification and detecting the label.

The foregoing disclosure is intended to illustrate the invention and is not to be construed as limiting its scope as defined by the appended claims. Upon reading the present disclosure, certain equivalents and variations will be apparent to one skilled in the art without exercise of inventive skill. Such equivalents and variations are intended to be included within the scope of the invention.

What is claimed is:

1. A method for detecting human restrictin in a sample comprising combining the sample with an antibody which binds to the protein fragment encoded by the 206/207N fragment of human restrictin, said 206/207N fragment consisting of nucleotides 2686–3165 of SEQ ID NO: 3, and detecting binding of the antibody to the human restrictin, thereby detecting the human restrictin in the sample.

2. The method of claim 1 wherein the human restrictin is detected in tissue.

3. The method of claim 1 wherein the human restrictin is detected in a cell or tissue extract.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

ACTGACAGAT CTAGAGCC        18

( 2 ) INFORMATION FOR SEQ ID NO:2:

( i ) SEQUENCE CHARACTERISTICS:

(A) LENGTH: 18 base pairs
(B) TYPE: nucleic acid
(C) STRANDEDNESS: single
(D) TOPOLOGY: linear (x i) SEQUENCE DESCRIPTION: SEQ ID NO:2:

| GGTGGTCGAT AGGATACT | | | | | 18 |
|---|---|---|---|---|---|

(2) INFORMATION FOR SEQ ID NO:3:

(i) SEQUENCE CHARACTERISTICS:
(A) LENGTH: 4724 base pairs
(B) TYPE: nucleic acid
(C) STRANDEDNESS: double
(D) TOPOLOGY: linear (ii) MOLECULE TYPE: cDNA (x i) SEQUENCE DESCRIPTION: SEQ ID NO:3:

| GAATTCCGGG | AGAAGGGGGT | CCTCTCTGAC | CCAAGGAATT | ACCACTAGTG | GAGTGAAGCC | 60 |
|---|---|---|---|---|---|---|
| ACCTGACTTT | TTGATCTTAT | TTGGTTGCC | TCCTCATTCT | CCTTCCACCC | GTAGCCCTGA | 120 |
| CAGCTTGGGT | TTCATTTCTT | TCGTGGAGCC | TTGTCTCTTC | CTCCCAGAAT | AGGAGGAAGG | 180 |
| GAAGAGAAGG | GAAAGAGGAG | GGCTCTCTAG | GTGAGCGCAT | CAGCTGGCTC | CAGCCTGAGC | 240 |
| AAGCAAGAAT | TTTCTTCCCA | GGAAGCTCCT | CTCGCTCCCC | GGCCGCCCAC | CCCCAGCCTG | 300 |
| GGTGGCTGTA | TCGTTTTAAC | TGCATAGAGG | GCAGGTCTCT | TTTGGAATTA | GGATTAAAGA | 360 |
| AAGTGCAGTA | AAGAGAAAGC | ATCGAAGACA | CCATCACAAA | AGATTCCCAC | AACTCCATGC | 420 |
| TGTGTGCTGC | AGGCTGGTCC | TGAACCCAGA | TCTCTGGCTG | AGAGGATGGG | GGCAGATGGG | 480 |
| GAAACAGTGG | TTCTGAAGAA | CATGCTCATT | GGCGTCAACC | TGATCCTTCT | GGGCTCCATG | 540 |
| ATCAAGCCTT | CAGAGTGTCA | GCTGGAGGTC | ACCACAGAAA | GGGTCCAGAG | ACAGTCAGTG | 600 |
| GAGGAGGAGG | GAGGCATTGC | CAACTACAAC | ACGTCCAGCA | AAGAGCAGCC | TGTGGTCTTC | 660 |
| AACCACGTGT | ACAACATTAA | CGTGCCCTTG | GACAACCTCT | GCTCCTCAGG | GCTAGAGGCC | 720 |
| TCTGCTGAGC | AGGAGGTGAG | TGCAGAAGAC | GAGACTCTGG | CAGAGTACAT | GGGCCAGACC | 780 |
| TCAGACCACG | AGAGCCAGGT | CACCTTTACA | CACAGGATCA | ACTTCCCCAA | AAAGGCCTGT | 840 |
| CCATGTTCCA | GTTCAGCCCA | GGTGCTGCAG | GAGCTGCTGA | GCCGGATCGA | GATGCTGGAG | 900 |
| AGGGAGGTGT | CGGTGCTGCG | AGACCAGTGC | AACGCCAACT | GCTGCCAAGA | AAGTGCTGCC | 960 |
| ACAGGACAAC | TGGACTATAT | CCCTCACTGC | AGTGGCCACG | GCAACTTTAG | CTTTGAGTCC | 1020 |
| TGTGGCTGCA | TCTGCAACGA | AGGCTGGTTT | GGCAAGAATT | GCTCGGAGCC | CTACTGCCCG | 1080 |
| CTGGGTTGCT | CCAGCCGGGG | GGTGTGTGTG | GATGGCCAGT | GCATCTGTGA | CAGCGAGTAC | 1140 |
| AGCGGGGATG | ACTGTTCCGA | ACTCCGGTGC | CCAACAGACT | GCAGCTCCCG | GGGGCTCTGC | 1200 |
| GTGGACGGGG | AGTGTGTCTG | TGAAGAGCCC | TACACTGGCG | AGGACTGCAG | GGAACTGAGG | 1260 |
| TGCCCTGGGG | ACTGTTCGGG | GAAGGGGAGA | TGTGCCACCG | GTACCTGTTT | ATGCGAGGAG | 1320 |
| GGCTACGTTG | GTGAGGACTG | CGGCCAGCGG | CAGTGTCTGA | ATGCCTGCAG | TGGGCGAGGA | 1380 |
| CAATGTGAGG | AGGGGCTCTG | CGTCTGTGAA | GAGGGCTACC | AGGGCCCTGA | CTGCTCAGCA | 1440 |
| GTTGCCCCTC | CAGAGGACTT | GCGAGTGGCT | GGTATCAGCG | ACAGGTCCAT | TGAGCTGGAA | 1500 |
| TGGGACGGGC | CGATGGCAGT | GACGGAATAT | GTGATCTCTT | ACCAGCCGAC | GGCCCTGGGG | 1560 |
| GGCCTCCAGC | TCCAGCAGCG | GGTGCCTGGA | GATTGGAGTG | GTGTCACCAT | CACGGAGCTG | 1620 |
| GAGCCAGGTC | TCACCTACAA | CATCAGCGTC | TACGCTGTCA | TTAGCAACAT | CCTCAGCCTT | 1680 |
| CCCATCACTG | CCAAGGTGGC | CACCCATCTC | TCCACTCCTC | AAGGGCTACA | ATTTAAGACG | 1740 |

```
ATCACAGAGA  CCACCGTGGA  GGTGCAGTGG  GAGCCCTTCT  CATTTTCCTT  CGATGGGTGG   1800
GAAATCAGCT  TCATTCCAAA  GAACAATGAA  GGGGGAGTGA  TTGCTCAGGT  CCCCAGCGAT   1860
GTTACGTCCT  TTAACCAGAC  AGGACTAAAG  CCTGGGGAGG  AATACATTGT  CAATGTGGTG   1920
GCTCTGAAAG  AACAGGCCCG  CAGCCCCCCT  ACCTCGGCCA  GCGTCTCCAC  AGTCATTGAC   1980
GGCCCCACGC  AGATCCTGGT  TCGCGATGTC  TCGGACACTG  TGGCTTTTGT  GGAGTGGATT   2040
CCCCCTCGAG  CCAAAGTCGA  TTTCATTCTT  TTGAAATATG  GCCTGGTGGG  CGGGGAAGGT   2100
GGGAGGACCA  CCTTCCGGCT  GCAGCCTCCC  CTGAGCCAAT  ACTCAGTGCA  GGCCCTGCGG   2160
CCTGGCTCCC  GATACGAGGT  GTCAGTCAGT  GCCGTCCGAG  GGACCAACGA  GAGCGATTCT   2220
GCCACCACTC  AGTTCACAAC  AGAGATCGAT  GCCCCAAGA   ACTTGCGAGT  TGGTTCTCGC   2280
ACAGCAACCA  GCCTTGACCT  CGAGTGGGAT  AACAGTGAAG  CCGAAGTTCA  GGAGTACAAG   2340
GTTGTGTACA  GCACCCTGGC  GGGTGAGCAA  TATCATGAGG  TACTGGTCCC  CAAGGGCATT   2400
GGTCCAACCA  CCAGGGCCAC  CCTGACAGAT  CTGGTACCTG  GCACTGAGTA  TGGAGTTGGA   2460
ATATCTGCCG  TCATGAACTC  ACAGCAAAGC  GTGCCAGCCA  CCATGAATGC  CAGGACTGAA   2520
CTTGACAGTC  CCCGAGACCT  CATGGTGACA  GCCTCCTCAG  AGACCTCCAT  CTCCCTCATC   2580
TGGACCAAGG  CCAGTGGCCC  CATTGACCAC  TACCGAATTA  CCTTTACCCC  ATCCTCTGGG   2640
ATTGCCTCAG  AAGTCACCGT  ACCCAAGGAC  AGGACCTCAT  ACACACTAAC  AGATCTAGAG   2700
CCTGGGGCAG  AGTACATCAT  TTCCGTCACT  GCTGAGAGGG  GTCGGCAGCA  GAGCTTGGAG   2760
TCCACTGTGG  ATGCTTTCAC  AGGCTTCCGT  CCCATCTCTC  ATCTGCACTT  TTCTCATGTG   2820
ACCTCCTCCA  GTGTGAACAT  CACTTGGAGT  GATCCATCTC  CCCCAGCAGA  CAGACTCATT   2880
CTTAACTACA  GCCCCAGGGA  TGAGGAGGAA  GAGATGATGG  AGGTCTCCCT  GGATGCCACC   2940
AAGAGGCATG  CTGTCCTGAT  GGGCCTGCAA  CCAGCCACAG  AGTATATTGT  GAACCTTGTG   3000
GCTGTCCATG  GCACAGTGAC  CTCTGAGCCC  ATTGTGGGCT  CCATCACCAC  AGGAATTGAT   3060
CCCCCAAAAG  ACATCACAAT  TAGCAATGTG  ACCAAGGACT  CAGTGATGGT  CTCCTGGAGC   3120
CCTCCTGTTG  CATCTTTCGA  TTACTACCGA  GTATCATATC  GACCCACCCA  AGTGGGACGA   3180
CTAGACAGCT  CAGTGGTGCC  CAACACTGTG  ACAGAATTCA  CCATCACCAG  ACTGAACCCA   3240
GCTACCGAAT  ACGAAATCAG  CCTCAACAGC  GTGCGGGGCA  GGGAGGAAAG  CGAGCGCATC   3300
TGTACTCTTG  TGCACACAGC  CATGGACAAC  CCTGTGGATC  TGATTGCTAC  CAATATCACT   3360
CCAACAGAAG  CCCTGCTGCA  GTGGAAGGCA  CCAGTGGGTG  AGGTGGAGAA  CTACGTCATT   3420
GTTCTTACAC  ACTTTGCAGT  CGCTGGAGAG  ACCATCCTTG  TTGACGGAGT  CAGTGAGGAA   3480
TTTCGGCTTG  TTGACCTGCT  TCCTAGCACC  CACTATACTG  CCACCATGTA  TGCCACCAAT   3540
GGACCTCTCA  CCAGTGGCAC  CATCAGCACC  AACTTTTCTA  CTCTCCTGGA  CCCTCCGGCA   3600
AACCTGACAG  CCAGTGAAGT  CACCAGACAA  AGTGCCCTGA  TCTCCTGGCA  GCCTCCCAGG   3660
GCAGAGATTG  AAAATTATGT  CTTGACCTAC  AAATCCACCG  ACGGAAGCCG  CAAGGAGCTG   3720
ATTGTGGATG  CAGAAGACAC  CTGGATTCGA  CTGGAGGGCC  TGTTGGAGAA  CACAGACTAC   3780
ACGGTGCTCC  TGCAGGCAAC  ACAGGACACC  ACGTGGAGCA  GCATCACCTC  CACCGCTTTC   3840
ACCACAGGAG  GCCGGGTGTT  CCCTCATCCC  CAAGACTGTG  CCAGCATTT   GATGAATGGA   3900
GACACTTTGA  GTGGGGTTTA  CCCCATCTTC  CTCAATGGGG  AGCTGAGCCA  GAAATTACAA   3960
GTGTACTGTG  ATATGACCAC  CGACGGGGGC  GGCTGGATTG  TATTCCAGAG  GCGGCAGAAT   4020
GGCCAAACTG  ATTTTTTCCG  GAAATGGGCT  GATTACCGTG  TTGGCTTCGG  GAACGTGGAG   4080
GATGAGTTCT  GGCTGGGGCT  GGACAATATA  CACAGGATCA  CATCCCAGGG  CCGCTATGAG   4140
```

-continued

```
CTGCGCGTGG ACATGCGGGA TGGCCAGGAG GCCGCCTTCG CCTCCTACGA CAGGTTCTCT    4200

GTCGAGGACA GCAGAAACCT GTACAAACTC CGCATAGGAA GCTACAACGG CACTGCGGGG    4260

GACTCCCTCA GCTATCATCA AGGACGCCCT TTCTCCACAG AGGATAGAGA CAATGATGTT    4320

GCAGTGACTA ACTGTGCCAT GTCGTACAAG GGAGCATGGT GGTATAAGAA CTGCCACCGG    4380

ACCAACCTCA ATGGGAAGTA CGGGGAGTCC AGGCACAGTC AGGGCATCAA CTGGTACCAT    4440

TGGAAAGGCC ATGAGTTCTC CATCCCCTTT GTGGAAATGA AGATGCGCCC CTACAACCAC    4500

CGTCTCATGG CAGGGAGAAA ACGGCAGTCC TTACAGTTCT GAGCAGTGGG CGGCTGCAAG    4560

CCAACCAATA TTTTCTGTCA TTTGTTTGTA TTTTATAATA TGAAACAAGG GGGGAGGGTA    4620

ATAGCAATGT TTTTTGCAAC ATATTAAGAG TATGTNAAGG AAGCAGGGAT GTCGCAGGAA    4680

TCCGCTGGCT AACATCTGCT CTNGGTTTCT GCTGNCCTGG AGGC                    4724
```

( 2 ) INFORMATION FOR SEQ ID NO:4:

( i ) SEQUENCE CHARACTERISTICS:
        ( A ) LENGTH: 1358 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met Gly Ala Asp Gly Glu Thr Val Val Leu Lys Asn Met Leu Ile Gly
  1               5                  10                  15

Val Asn Leu Ile Leu Leu Gly Ser Met Ile Lys Pro Ser Glu Cys Gln
             20                  25                  30

Leu Glu Val Thr Thr Glu Arg Val Gln Arg Gln Ser Val Glu Glu Glu
         35                  40                  45

Gly Gly Ile Ala Asn Tyr Asn Thr Ser Ser Lys Glu Gln Pro Val Val
     50                  55                  60

Phe Asn His Val Tyr Asn Ile Asn Val Pro Leu Asp Asn Leu Cys Ser
 65                  70                  75                  80

Ser Gly Leu Glu Ala Ser Ala Glu Gln Glu Val Ser Ala Glu Asp Glu
                 85                  90                  95

Thr Leu Ala Glu Tyr Met Gly Gln Thr Ser Asp His Glu Ser Gln Val
            100                 105                 110

Thr Phe Thr His Arg Ile Asn Phe Pro Lys Lys Ala Cys Pro Cys Ser
        115                 120                 125

Ser Ser Ala Gln Val Leu Gln Glu Leu Leu Ser Arg Ile Glu Met Leu
    130                 135                 140

Glu Arg Glu Val Ser Val Leu Arg Asp Gln Cys Asn Ala Asn Cys Cys
145                 150                 155                 160

Gln Glu Ser Ala Ala Thr Gly Gln Leu Asp Tyr Ile Pro His Cys Ser
                165                 170                 175

Gly His Gly Asn Phe Ser Phe Glu Ser Cys Gly Cys Ile Cys Asn Glu
            180                 185                 190

Gly Trp Phe Gly Lys Asn Cys Ser Glu Pro Tyr Cys Pro Leu Gly Cys
        195                 200                 205

Ser Ser Arg Gly Val Cys Val Asp Gly Gln Cys Ile Cys Asp Ser Glu
    210                 215                 220

Tyr Ser Gly Asp Asp Cys Ser Glu Leu Arg Cys Pro Thr Asp Cys Ser
225                 230                 235                 240

Ser Arg Gly Leu Cys Val Asp Gly Glu Cys Val Cys Glu Glu Pro Tyr
                245                 250                 255
```

```
Thr  Gly  Glu  Asp  Cys  Arg  Glu  Leu  Arg  Cys  Pro  Gly  Asp  Cys  Ser  Gly
               260                      265                     270

Lys  Gly  Arg  Cys  Ala  Thr  Gly  Thr  Cys  Leu  Cys  Glu  Glu  Gly  Tyr  Val
                    275                      280                290

Gly  Glu  Asp  Cys  Gly  Gln  Arg  Gln  Cys  Leu  Asn  Ala  Cys  Ser  Gly  Arg
          290                      295                     300

Gly  Gln  Cys  Glu  Glu  Gly  Leu  Cys  Val  Cys  Glu  Glu  Gly  Tyr  Gln  Gly
305                           310                     315                    320

Pro  Asp  Cys  Ser  Ala  Val  Ala  Pro  Pro  Glu  Asp  Leu  Arg  Val  Ala  Gly
                         325                330                     335

Ile  Ser  Asp  Arg  Ser  Ile  Glu  Leu  Glu  Trp  Asp  Gly  Pro  Met  Ala  Val
                    340                      345                     350

Thr  Glu  Tyr  Val  Ile  Ser  Tyr  Gln  Pro  Thr  Ala  Leu  Gly  Leu  Gln
               355                      360                     365

Leu  Gln  Gln  Arg  Val  Pro  Gly  Asp  Trp  Ser  Gly  Val  Thr  Ile  Thr  Glu
     370                      375                     380

Leu  Glu  Pro  Gly  Leu  Thr  Tyr  Asn  Ile  Ser  Val  Tyr  Ala  Val  Ile  Ser
385                      390                     395                         400

Asn  Ile  Leu  Ser  Leu  Pro  Ile  Thr  Ala  Lys  Val  Ala  Thr  His  Leu  Ser
                    405                      410                     415

Thr  Pro  Gln  Gly  Leu  Gln  Phe  Lys  Thr  Ile  Thr  Glu  Thr  Thr  Val  Glu
               420                      425                     430

Val  Gln  Trp  Glu  Pro  Phe  Ser  Phe  Ser  Phe  Asp  Gly  Trp  Glu  Ile  Ser
               435                      440                     445

Phe  Ile  Pro  Lys  Asn  Asn  Glu  Gly  Gly  Val  Ile  Ala  Gln  Val  Pro  Ser
     450                      455                     460

Asp  Val  Thr  Ser  Phe  Asn  Gln  Thr  Gly  Leu  Lys  Pro  Gly  Glu  Glu  Tyr
465                      470                     475                         480

Ile  Val  Asn  Val  Val  Ala  Leu  Lys  Glu  Gln  Ala  Arg  Ser  Pro  Pro  Thr
                         485                      490                     495

Ser  Ala  Ser  Val  Ser  Thr  Val  Ile  Asp  Gly  Pro  Thr  Gln  Ile  Leu  Val
               500                      505                     510

Arg  Asp  Val  Ser  Asp  Thr  Val  Ala  Phe  Val  Glu  Trp  Ile  Pro  Pro  Arg
          515                      520                     525

Ala  Lys  Val  Asp  Phe  Ile  Leu  Leu  Lys  Tyr  Gly  Leu  Val  Gly  Gly  Glu
     530                      535                     540

Gly  Gly  Arg  Thr  Thr  Phe  Arg  Leu  Gln  Pro  Pro  Leu  Ser  Gln  Tyr  Ser
545                           550                     555                    560

Val  Gln  Ala  Leu  Arg  Pro  Gly  Ser  Arg  Tyr  Glu  Val  Ser  Val  Ser  Ala
                    565                      570                     575

Val  Arg  Gly  Thr  Asn  Glu  Ser  Asp  Ser  Ala  Thr  Thr  Gln  Phe  Thr  Thr
               580                      585                     590

Glu  Ile  Asp  Ala  Pro  Lys  Asn  Leu  Arg  Val  Gly  Ser  Arg  Thr  Ala  Thr
          595                      600                     605

Ser  Leu  Asp  Leu  Glu  Trp  Asp  Asn  Ser  Glu  Ala  Glu  Val  Gln  Glu  Tyr
     610                      615                     620

Lys  Val  Val  Tyr  Ser  Thr  Leu  Ala  Gly  Glu  Gln  Tyr  His  Glu  Val  Leu
625                      630                     635                         640

Val  Pro  Lys  Gly  Ile  Gly  Pro  Thr  Thr  Arg  Ala  Thr  Leu  Thr  Asp  Leu
                    645                      650                     655

Val  Pro  Gly  Thr  Glu  Tyr  Gly  Val  Gly  Ile  Ser  Ala  Val  Met  Asn  Ser
               660                      665                     670

Gln  Gln  Ser  Val  Pro  Ala  Thr  Met  Asn  Ala  Arg  Thr  Glu  Leu  Asp  Ser
```

-continued

```
              675                      680                      685
Pro  Arg  Asp  Leu  Met  Val  Thr  Ala  Ser  Ser  Glu  Thr  Ser  Ile  Ser  Leu
          690                      695                      700
Ile  Trp  Thr  Lys  Ala  Ser  Gly  Pro  Ile  Asp  His  Tyr  Arg  Ile  Thr  Phe
705                      710                      715                      720
Thr  Pro  Ser  Ser  Gly  Ile  Ala  Ser  Glu  Val  Thr  Val  Pro  Lys  Asp  Arg
                    725                      730                      735
Thr  Ser  Tyr  Thr  Leu  Thr  Asp  Leu  Glu  Pro  Gly  Ala  Glu  Tyr  Ile  Ile
                    740                      745                      750
Ser  Val  Thr  Ala  Glu  Arg  Gly  Arg  Gln  Gln  Ser  Leu  Glu  Ser  Thr  Val
               755                      760                      765
Asp  Ala  Phe  Thr  Gly  Phe  Arg  Pro  Ile  Ser  His  Leu  His  Phe  Ser  His
     770                      775                      780
Val  Thr  Ser  Ser  Ser  Val  Asn  Ile  Thr  Trp  Ser  Asp  Pro  Ser  Pro  Pro
785                      790                      795                      800
Ala  Asp  Arg  Leu  Ile  Leu  Asn  Tyr  Ser  Pro  Arg  Asp  Glu  Glu  Glu  Glu
                    805                      810                      815
Met  Met  Glu  Val  Ser  Leu  Asp  Ala  Thr  Lys  Arg  His  Ala  Val  Leu  Met
               820                      825                      830
Gly  Leu  Gln  Pro  Ala  Thr  Glu  Tyr  Ile  Val  Asn  Leu  Val  Ala  Val  His
          835                      840                      845
Gly  Thr  Val  Thr  Ser  Glu  Pro  Ile  Val  Gly  Ser  Ile  Thr  Thr  Gly  Ile
     850                      855                      860
Asp  Pro  Pro  Lys  Asp  Ile  Thr  Ile  Ser  Asn  Val  Thr  Lys  Asp  Ser  Val
865                      870                      875                      880
Met  Val  Ser  Trp  Ser  Pro  Pro  Val  Ala  Ser  Phe  Asp  Tyr  Tyr  Arg  Val
                    885                      890                      895
Ser  Tyr  Arg  Pro  Thr  Gln  Val  Gly  Arg  Leu  Asp  Ser  Ser  Val  Val  Pro
               900                      905                      910
Asn  Thr  Val  Thr  Glu  Phe  Thr  Ile  Thr  Arg  Leu  Asn  Pro  Ala  Thr  Glu
          915                      920                      925
Tyr  Glu  Ile  Ser  Leu  Asn  Ser  Val  Arg  Gly  Arg  Glu  Glu  Ser  Glu  Arg
     930                      935                      940
Ile  Cys  Thr  Leu  Val  His  Thr  Ala  Met  Asp  Asn  Pro  Val  Asp  Leu  Ile
945                      950                      955                      960
Ala  Thr  Asn  Ile  Thr  Pro  Thr  Glu  Ala  Leu  Leu  Gln  Trp  Lys  Ala  Pro
                    965                      970                      975
Val  Gly  Glu  Val  Glu  Asn  Tyr  Val  Ile  Val  Leu  Thr  His  Phe  Ala  Val
               980                      985                      990
Ala  Gly  Glu  Thr  Ile  Leu  Val  Asp  Gly  Val  Ser  Glu  Glu  Phe  Arg  Leu
          995                      1000                     1005
Val  Asp  Leu  Leu  Pro  Ser  Thr  His  Tyr  Thr  Ala  Thr  Met  Tyr  Ala  Thr
     1010                     1015                     1020
Asn  Gly  Pro  Leu  Thr  Ser  Gly  Thr  Ile  Ser  Thr  Asn  Phe  Ser  Thr  Leu
1025                     1030                     1035                     1040
Leu  Asp  Pro  Pro  Ala  Asn  Leu  Thr  Ala  Ser  Glu  Val  Thr  Arg  Gln  Ser
                    1045                     1050                     1055
Ala  Leu  Ile  Ser  Trp  Gln  Pro  Pro  Arg  Ala  Glu  Ile  Glu  Asn  Tyr  Val
               1060                     1065                     1070
Leu  Thr  Tyr  Lys  Ser  Thr  Asp  Gly  Ser  Arg  Lys  Glu  Leu  Ile  Val  Asp
          1075                     1080                     1085
Ala  Glu  Asp  Thr  Trp  Ile  Arg  Leu  Glu  Gly  Leu  Leu  Glu  Asn  Thr  Asp
     1090                     1095                     1100
```

```
Tyr Thr Val Leu Leu Gln Ala Thr Gln Asp Thr Thr Trp Ser Ser Ile
1105                1110            1115                 1120

Thr Ser Thr Ala Phe Thr Thr Gly Gly Arg Val Phe Pro His Pro Gln
                1125            1130             1135

Asp Cys Ala Gln His Leu Met Asn Gly Asp Thr Leu Ser Gly Val Tyr
                1140             1145             1150

Pro Ile Phe Leu Asn Gly Glu Leu Ser Gln Lys Leu Gln Val Tyr Cys
        1155             1160             1165

Asp Met Thr Thr Asp Gly Gly Gly Trp Ile Val Phe Gln Arg Arg Gln
        1170             1175            1180

Asn Gly Gln Thr Asp Phe Phe Arg Lys Trp Ala Asp Tyr Arg Val Gly
1185                1190             1195            1200

Phe Gly Asn Val Glu Asp Glu Phe Trp Leu Gly Leu Asp Asn Ile His
                1205             1210            1215

Arg Ile Thr Ser Gln Gly Arg Tyr Glu Leu Arg Val Asp Met Arg Asp
                1220             1225            1230

Gly Gln Glu Ala Ala Phe Ala Ser Tyr Asp Arg Phe Ser Val Glu Asp
        1235             1240            1245

Ser Arg Asn Leu Tyr Lys Leu Arg Ile Gly Ser Tyr Asn Gly Thr Ala
    1250             1255            1260

Gly Asp Ser Leu Ser Tyr His Gln Gly Arg Pro Phe Ser Thr Glu Asp
1265            1270            1275            1280

Arg Asp Asn Asp Val Ala Val Thr Asn Cys Ala Met Ser Tyr Lys Gly
                1285            1290            1295

Ala Trp Trp Tyr Lys Asn Cys His Arg Thr Asn Leu Asn Gly Lys Tyr
            1300            1305            1310

Gly Glu Ser Arg His Ser Gln Gly Ile Asn Trp Tyr His Trp Lys Gly
        1315            1320            1325

His Glu Phe Ser Ile Pro Phe Val Glu Met Lys Met Arg Pro Tyr Asn
    1330            1335            1340

His Arg Leu Met Ala Gly Arg Lys Arg Gln Ser Leu Gln Phe
1345            1350            1355
```